(12) United States Patent
Sugimoto et al.

(10) Patent No.: US 8,728,097 B1
(45) Date of Patent: May 20, 2014

(54) TISSUE PLICATION DEVICES AND METHODS FOR THEIR USE

(75) Inventors: Hiroatsu Sugimoto, Cambridge, MA (US); Joseph P. Lane, Methuen, MA (US)

(73) Assignee: Mitralign, Inc., Tewksbury, MA (US)

( * ) Notice: Subject to any disclaimer, the term of this patent is extended or adjusted under 35 U.S.C. 154(b) by 579 days.

(21) Appl. No.: 12/393,608

(22) Filed: Feb. 26, 2009

Related U.S. Application Data

(60) Provisional application No. 61/031,426, filed on Feb. 26, 2008.

(51) Int. Cl.
*A61F 2/24* (2006.01)

(52) U.S. Cl.
USPC ........................................................ 606/142

(58) Field of Classification Search
USPC ................ 606/142, 151, 146; 623/2.14, 2.36, 623/2.42; 600/37
See application file for complete search history.

(56) References Cited

U.S. PATENT DOCUMENTS

| | | | |
|---|---|---|---|
| 6,663,633 B1 * | 12/2003 | Pierson, III | 606/148 |
| 2003/0216693 A1 * | 11/2003 | Mickley | 604/164.01 |
| 2006/0015002 A1 * | 1/2006 | Moaddeb et al. | 600/37 |
| 2007/0244555 A1 * | 10/2007 | Rafiee et al. | 623/2.11 |

* cited by examiner

*Primary Examiner* — Ryan Severson
*Assistant Examiner* — Anh Dang
(74) *Attorney, Agent, or Firm* — Leason Ellis LLP

(57) ABSTRACT

A tissue plication device and method of using the same is described. The tissue plication device includes a helical fastener having a distal portion with a first pitch and a proximal portion with a second pitch that is smaller than the first pitch. The method includes introducing the distal tip of the helical fastener into the tissue and advancing the helical fastener to plicate the tissue. Another tissue plication device includes a helical fastener having a first configuration with a first pitch and a second configuration with a second pitch. The helical fastener in the first configuration is advanced into a tissue and then converted to the second configuration by applying a stimulus.

23 Claims, 9 Drawing Sheets

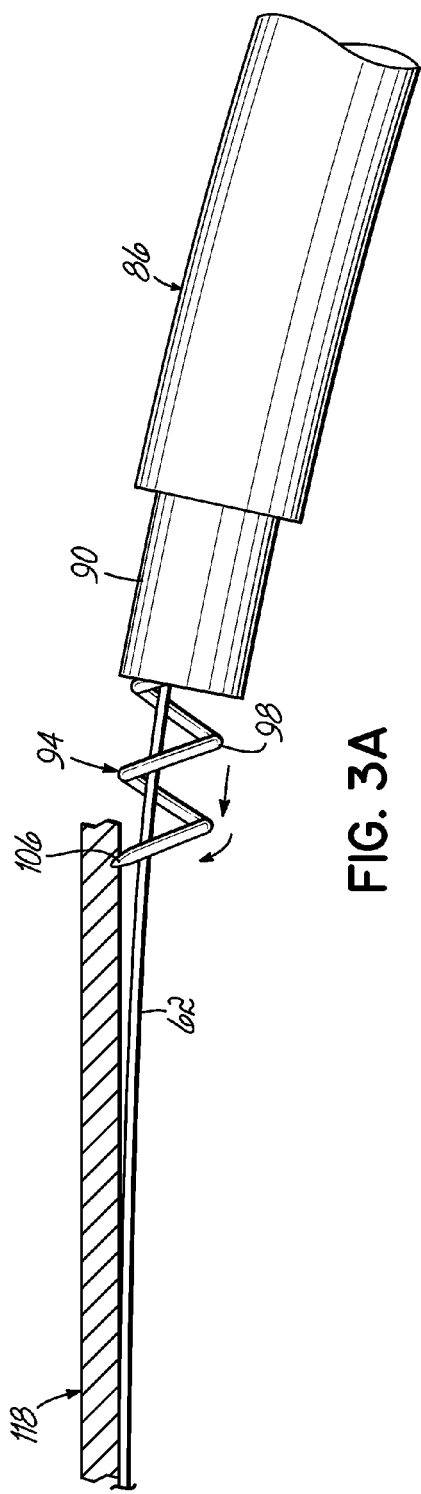
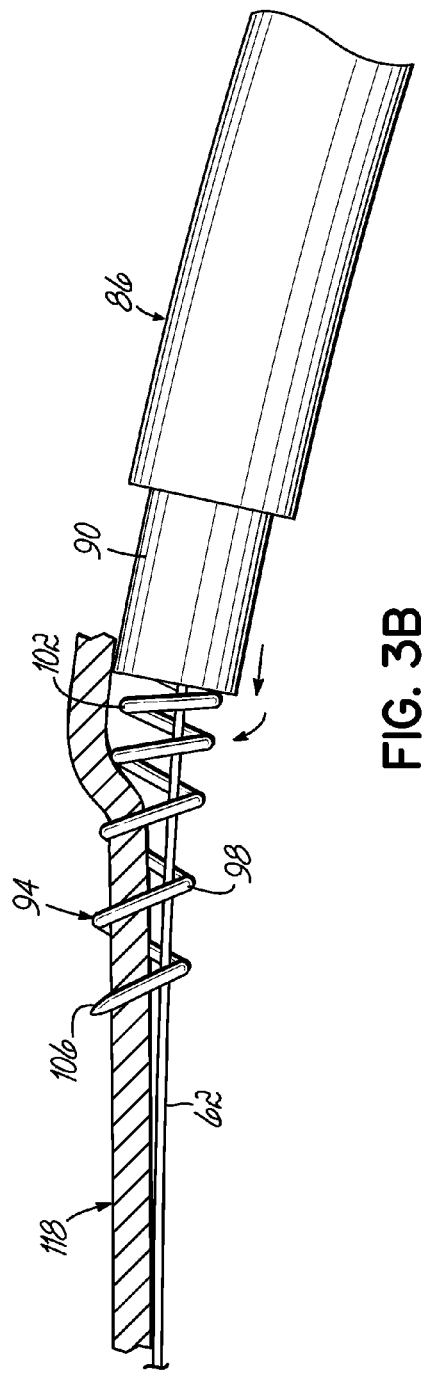
FIG. 3A
FIG. 3B

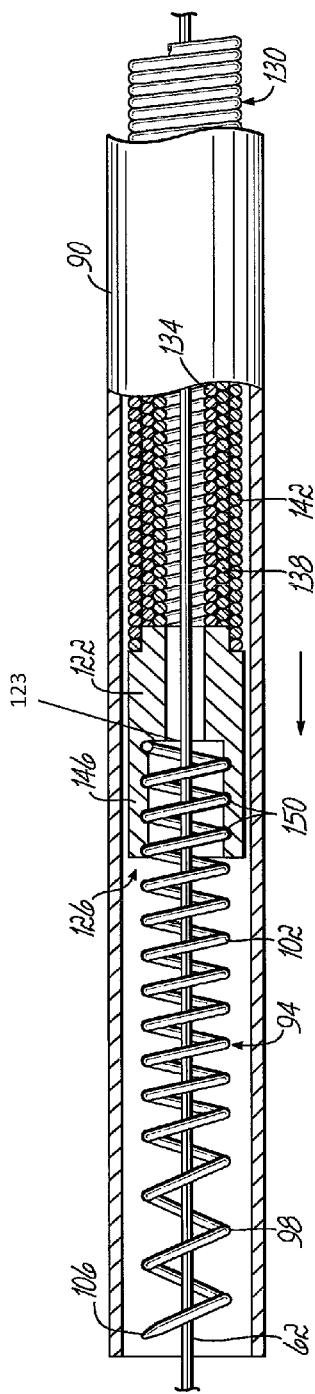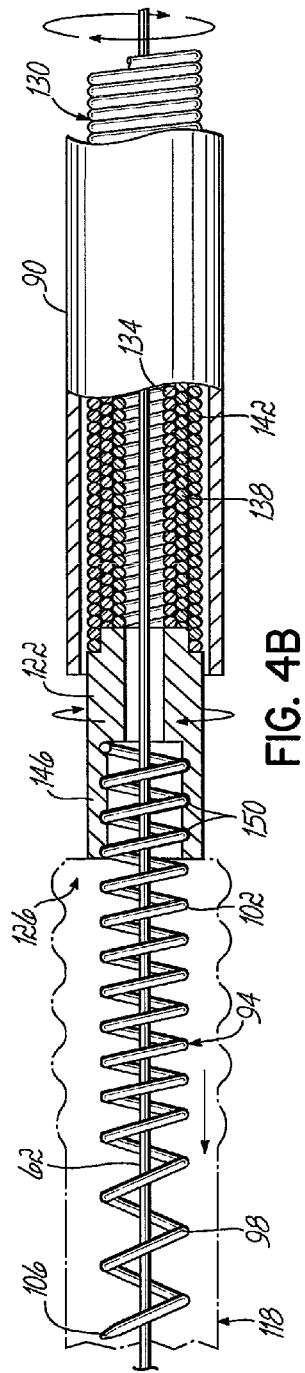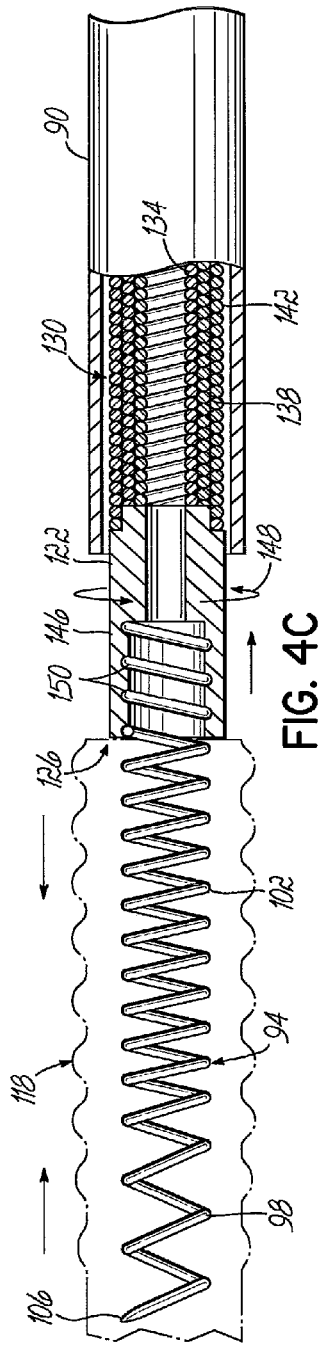

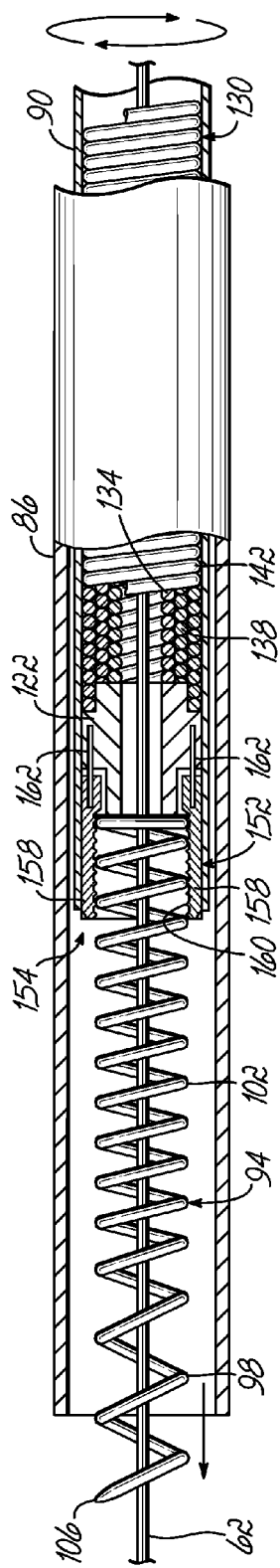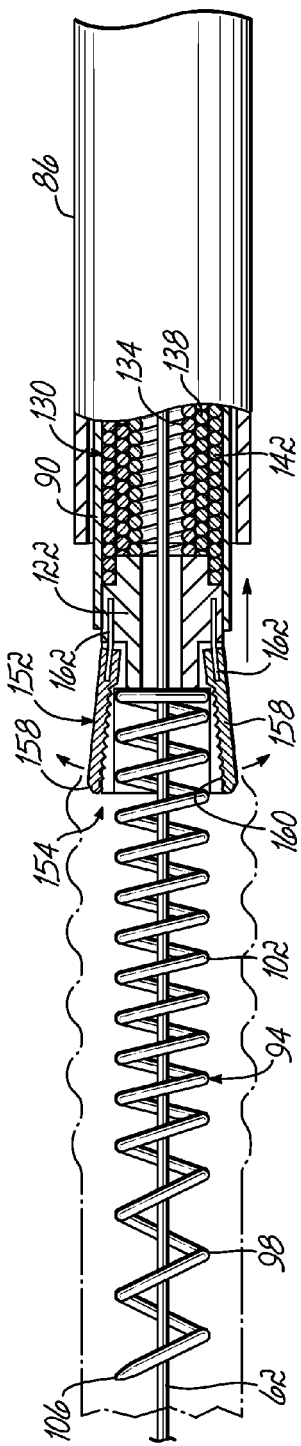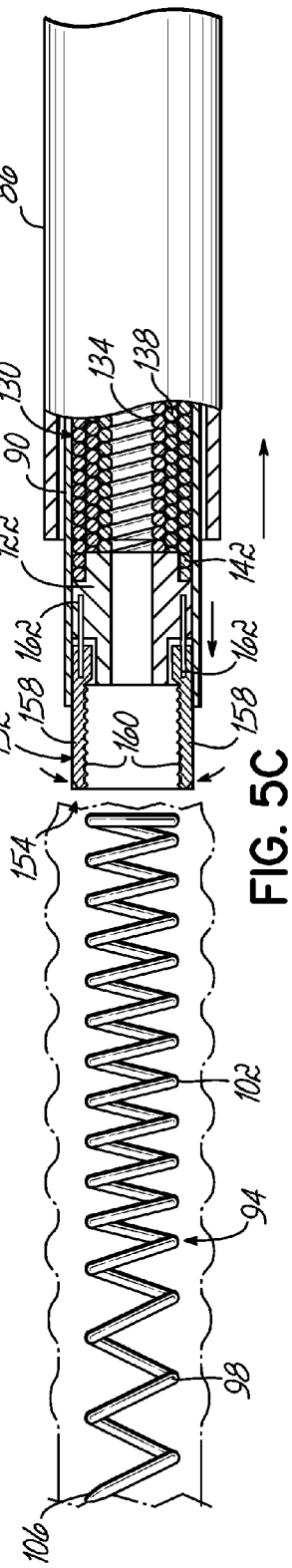

TISSUE PLICATION DEVICES AND METHODS FOR THEIR USE

This application claims the priority of U.S. Provisional Patent Application Ser. No. 61/031,426, filed on Feb. 26, 2008 the disclosure of which is incorporated by reference herein.

TECHNICAL FIELD

The present invention generally relates to tissue plication devices and a manner of using the same for plicating a tissue and, more particularly, to tissue plication devices for reducing a circumferential opening within a tissue.

BACKGROUND

The mitral valve is composed of valve leaflets, or flaps of tissue, that open and close tightly to ensure that the flow of blood through the heart is in one direction only. The leaflets are held in position by a ring of tissue, the annulus, surrounding and attaching the leaflets to the walls of the heart between the left atrium and left ventricle. Chordae tendineae are tendons that tether the leaflets to papillary muscles within the left ventricle, which prevent the leaflets from prolapsing into the left atrium. A dysfunction of any one of these portions of the mitral valve anatomy can cause mitral regurgitation, or the partial backflow of blood from the left ventricle into the left atrium. Depending on the severity of the condition, the individual may experience a range of symptoms including shortness of breath, pulmonary edema, or decreased exercise tolerance.

Surgical procedures may be used for reducing mitral regurgitation. Some of these procedures have included plicating the mitral valve tissue in order to reduce the size of the opening created between the leaflets. One such surgical procedure, annuloplasty, is particularly useful in treating mitral valve regurgitation. Annuloplasty modifies the annulus, through one or more plications, and this can return the valve to a functional geometry.

However, many annuloplasty procedures are highly invasive and may incorporate open heart surgery, posing significant risk to the patient. Therefore, there is a need for a less invasive approach for plicating tissue by eliminating the need for open heart surgery while returning the mitral valve to a functional geometry.

SUMMARY

In one illustrative embodiment of the present invention, a method of plicating a tissue is described. The method uses a helical fastener having a distal portion with a first pitch and a proximal portion with a second pitch that is smaller than the first pitch. The method includes introducing the distal tip of the helical fastener into the tissue and advancing the distal portion into the tissue. Continued advancing causes the proximal portion of the helical fastener to occupy a space that was previously occupied by the distal portion, which plicates the tissue.

In another illustrative method of plicating tissue, a helical fastener having a first configuration with a first pitch is introduced and advanced into the tissue. The helical fastener is then converted from the first configuration to a second configuration by applying a stimulus to the helical fastener. The second configuration has a pitch that is smaller than the first configuration, and the fastener plicates the tissue in the second configuration.

Another illustrative method of plicating tissue includes a helical fastener having a first configuration with a first pitch and a second configuration with a second pitch. The second pitch is greater than the first pitch. The helical faster is converted from the first configuration to the second configuration and then introduced into the tissue. After the helical faster has been advanced into the tissue, the helical fastener is then converted back to the first configuration, which plicates the tissue.

In another illustrative embodiment, the present invention is directed to a helical fastener having a distal portion with a first pitch and a proximal portion with a second pitch that is smaller than the first pitch.

Another illustrative embodiment of the present invention is directed to a coil deployment device for delivering the tissue plication device to a tissue. The coil deployment device includes a torque coil and a hub coupled to the distal end of the torque coil. The hub has a distal end that receives the proximal portion of the helical fastener.

BRIEF DESCRIPTION OF THE DRAWINGS

FIGS. 3A-3E are elevational views illustrating an exemplary method of directing the helical fastener into a tissue and thereby plicating the tissue.

FIGS. 4A-4C are side-elevational views, in partial cross-section, of an exemplary embodiment of a coil deployment device and a method of using the same.

FIGS. 5A-5C are side-elevational views, in partial cross-section, of an alternative embodiment of a coil deployment device and a method of using the same.

DETAILED DESCRIPTION

Figure 1A:
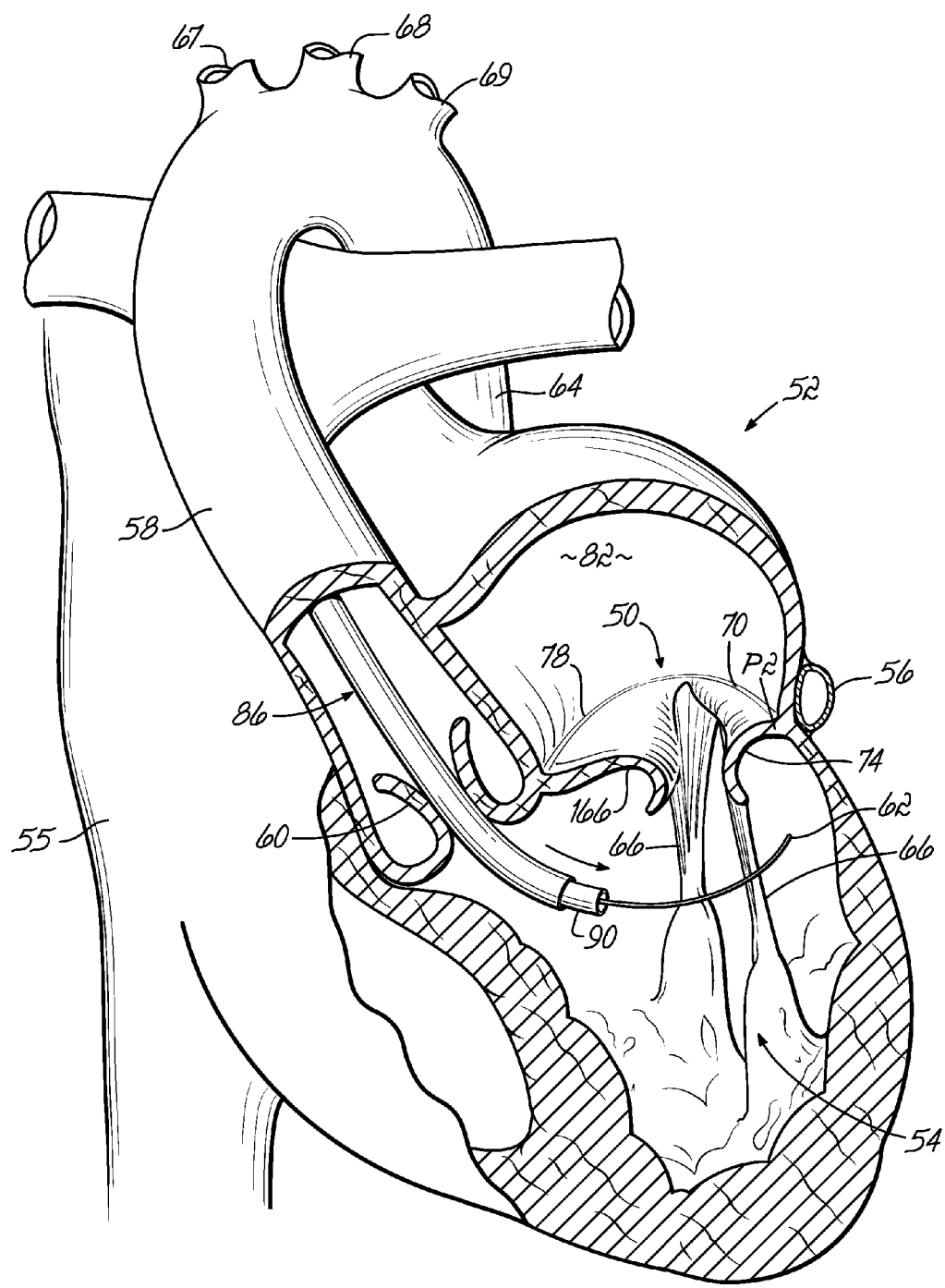
FIGS. 1A-1B are fragmentary cross-sectional views illustrating one exemplary procedure for advancing a guide-wire to the mitral valve.

Implanting a tissue plication device can begin with percutaneously accessing the tissue in a known manner. For example, FIG. 1A illustrates accessing the mitral valve 50 of the heart 52 from the left ventricle 54. The left ventricle 54 can be percutaneously accessed through the aortic arch 58 from a suitable arterial access site, such as the femoral or iliac arteries. Accordingly, the physician creates an incision sufficiently near the suitable artery and directs a guide-wire 62 through the arterial access site, up the aorta 64, around the aortic arch 58, through the aortic valve 60, and between the pair of chordae tendineae 66 in the left ventricle 54.

Alternatively, the percutaneous access can be made from a superior arterial access site such that the tissue plication device is directed into the aortic arch 58 from the brachiocephalic trunk 67, the left common carotid 68, or the left subclavian arteries 69. In yet other embodiments, the tissue plication device is directed into the heart 52 from a venous access site through the vena cava 55 or the coronary sinus 56.

With the guide-wire 62 within the left ventricle 54, the physician can then steer the guide-wire 62 toward the posterior annulus 70 of the mitral valve 50. As shown, the guide-wire 62 enters the mitral valve tissue near the P2 region located medially at the base of the posterior leaflet 74 along the posterior annulus 70; however, in some embodiments it may be preferred for the guide-wire 62 to be inserted into the posterior annulus 70 near the P1 region though this is not specifically shown.

After the guide-wire 62 is located within the left ventricle 54, a guide catheter 86 can then be directed over the guide-wire 62. The guide catheter 86 can be any suitable catheter that can be directed through the vascular system to aid in the delivery of subsequent surgical devices to the surgical site. The tissue plication device (described below) with a delivery sheath 90 can then be directed over the guide-wire 62 and through the lumen of the guide catheter 86 to the surgical site.

Figure 1B:
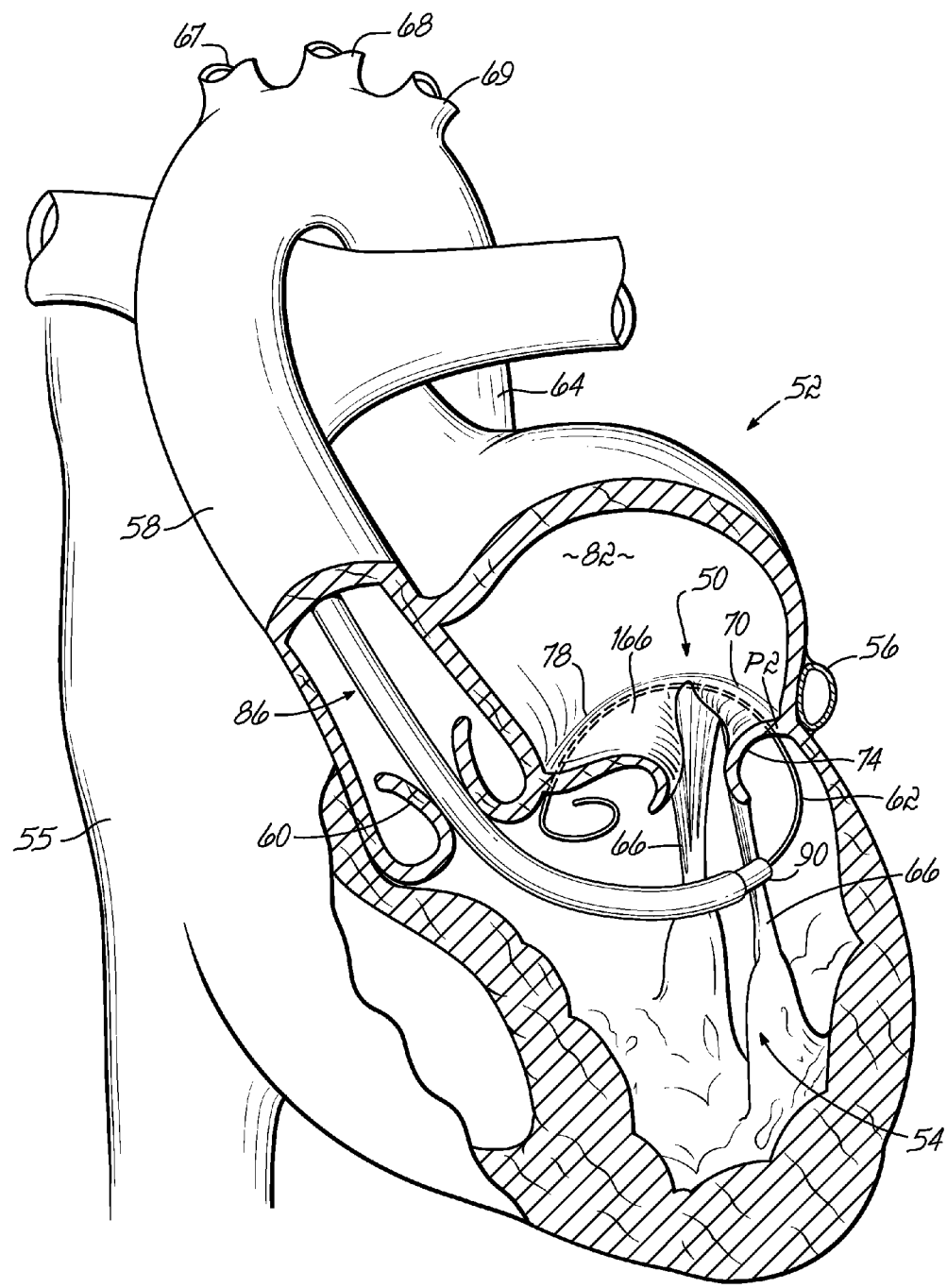

To ensure proper positioning of the guide-wire 62 at the mitral valve 50, the guide-wire 62 can include at least one fluoroscopic marker that allows for in vivo localization. The physician can then steer the distal tip of the guide-wire 62 into the P2 region and around the posterior annulus 70, as shown in FIG. 1B. In some embodiments, the guide-wire 62 further includes a radio-frequency (RF) energy delivery tip for assisting with penetration through the mitral tissue. For this purpose, a suitable RF energy device (not shown) may be coupled to the guide-wire 62.

While this embodiment of the invention is illustrated with the guide-wire 62 extending from the P2 and P3 regions to the anterior annulus 78, it would be understood that other positions on the mitral valve 50 could also receive the guide-wire 62. Additionally, the specific regions traversed should not be considered so limited. While the tissue plication device (described below) is illustrated for use with the mitral valve 50 from within the left ventricle 54, it would be understood that similar procedures and techniques could be used for directing and inserting the tissue plication device from within the left atrium 82 or from the circumflex artery (not shown).

Figure 2A:
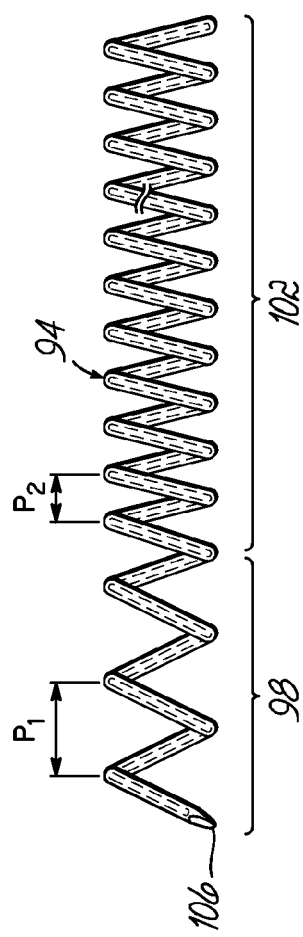
FIGS. 2A-2B are elevational views of two exemplary embodiments of helical fasteners.

Turning now to FIG. 2, where the details of one embodiment of the tissue plication device are shown in greater detail. The tissue plication device can be a helical fastener 94 having a distal portion 98 with a first pitch, $P_1$, and a proximal portion 102 with a second pitch, $P_2$, that is smaller than the first pitch. Explained another way, the proximal portion 102 will have a greater number of coils per unit of distance as compared with the distal portion 98. Preferably, the first pitch can be about 5.08 mm (0.200 inches) and the second pitch can range from about 1.27 mm (0.050 inches) to about 2.54 mm (0.100 inches); however, these dimensions should not be considered limiting.

The helical fastener 94 can be constructed from metals or metallic alloys, such as stainless steel, titanium, platinum, and nickel titanium; or from non-metal polymer materials such as polyetherimide, polyimide, polyester, and polyolefins, or from any other suitable bio-compatible material(s). In some embodiments, the metal or non-metal construction can be further coated with polytetrafluoroethylene polymer (PTFE) to reduce the frictional coefficient of the helical fastener 94.

The helical fastener 94 can be formed on a spring winder where the metal or non-metal material is wound around a mandrel having the desired diameter. The material is supplied from a moveable carriage to the mandrel at a first speed to create the first pitch; a second speed of the moveable carriage creates the second pitch. Alternatively, the helical fastener 94 can be manufactured by winding the desired material around a fixture having the desired geometry. Once winding of the material is complete, the helical fastener 94 is released from the fixture and heat treated into the desired configuration.

The distal end of the helical fastener 94 can be shaped into a distal tip 106 for penetrating or cutting through tissue. Accordingly, the distal tip 106 can be a sharpened point, knife-like, or other known shapes. Shaping of the distal tip 106 of the helical fastener 94 can be accomplished after the winding by heat treatment, grinding, or other means.

Figure 2B:
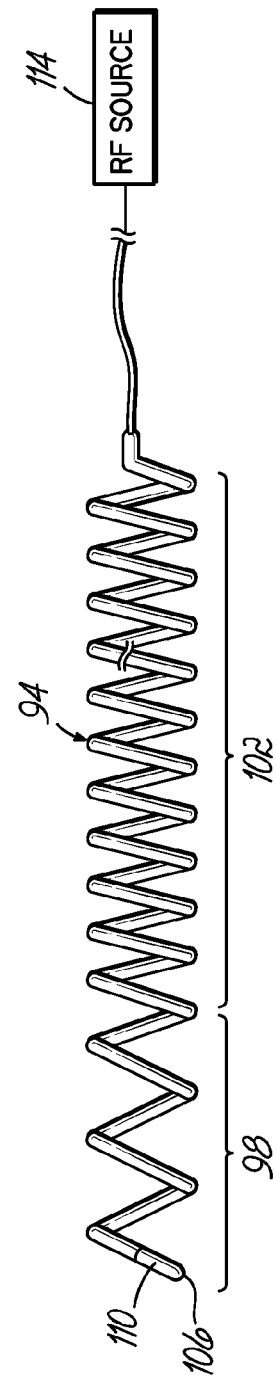

In some embodiments, such as the illustrative embodiment of FIG. 2B, the distal tip 106 can include a radio-frequency ablation tip 110, which is coupled to a remote radio-frequency energy source 114. The radio-frequency energy source 114 provides a radio-frequency energy to the ablation tip 110 of the distal tip 106 that is sufficient to burn through, or cauterize, tissue while the distal tip 106 is advancing into the tissue. The cauterizing of tissue can aid in the movement of the helical fastener 94 through the tissue and, in some instances, reduce bleeding.

Figure 3C:
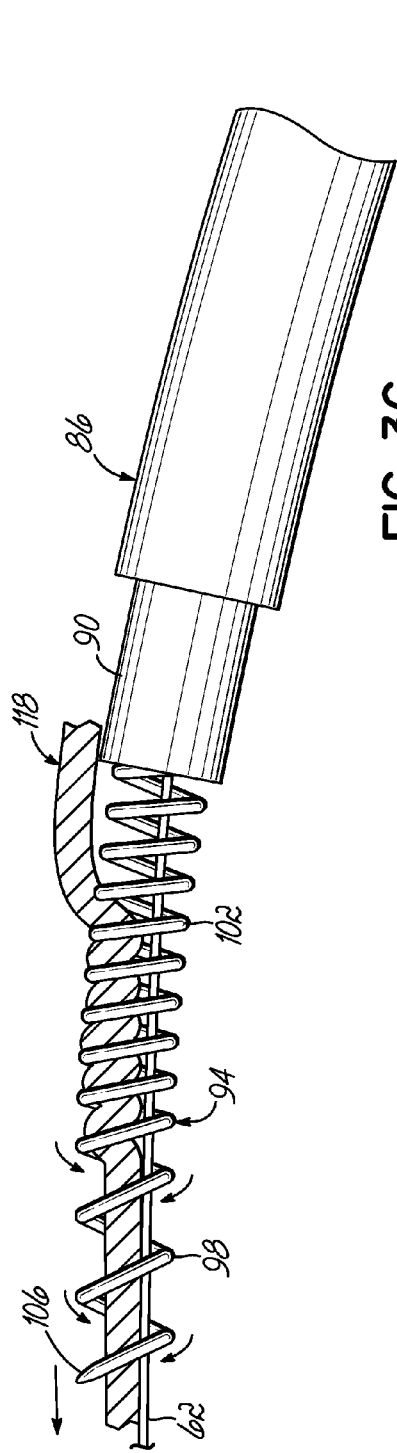

With the details described, the method of implanting the helical fastener 94 can continue with reference to FIGS. 3A-3E. Once the helical fastener 94 and the delivery sheath 90 have been advanced through the lumen of the guide catheter 86 to the surgical site, the distal tip 106 is advanced so that it emerges slightly from the distal end of the delivery sheath 90 and contacts the tissue 118, as shown in FIG. 3A. By rotating the helical fastener 94 out of the delivery sheath 90, the helical fastener 94 is advanced into a tissue 118, as shown in FIG. 3B. It is generally preferred that the helical fastener 94 threads itself along the curvature of the tissue 118, which can be accomplished by positioning the guide-wire 62 along the tissue 118 as a guide. In yet other embodiments, the helical fastener 94 is preformed with shape memory material to have the desired end-result shape for the tissue 118. As the preformed helical fastener 94 is advanced into the tissue 118, it would follow its predetermined shape without the aid of the guide-wire 62.

While the illustrated embodiments may be described as introducing and advancing the helical fastener into the tissue, it would be understood that in some embodiments, such as the one illustrated here, the helical fastener 94 can at least partially extend around the tissue 118. However, alternative embodiments will also be described below where the introducing and advancing of the helical fastener 94 into the tissue 118 includes at least partially embedding the helical fastener 94 within the tissue.

FIG. 3C illustrates the continued advancement of the distal portion 98 of the helical fastener 94 into the tissue 118, which is followed with the proximal portion 102 causing the tissue 118 to plicate. The plication of the tissue 118 is due to the variable pitch along the length of the helical fastener 94. That is, as the helical fastener 94 is advanced along the tissue 118, the change in the pitch between the distal and proximal portions 98, 102 induces a localized compression of the tissue 118. As the proximal portion 102 is advanced to occupy a space that was previously occupied by the distal portion 98, the smaller pitch associated with the proximal portion 102 causes an increase stress in the tissue 118, biasing the tissue 118 to be plicated. This plication reduces the overall length of the tissue 118.

Figure 3D:
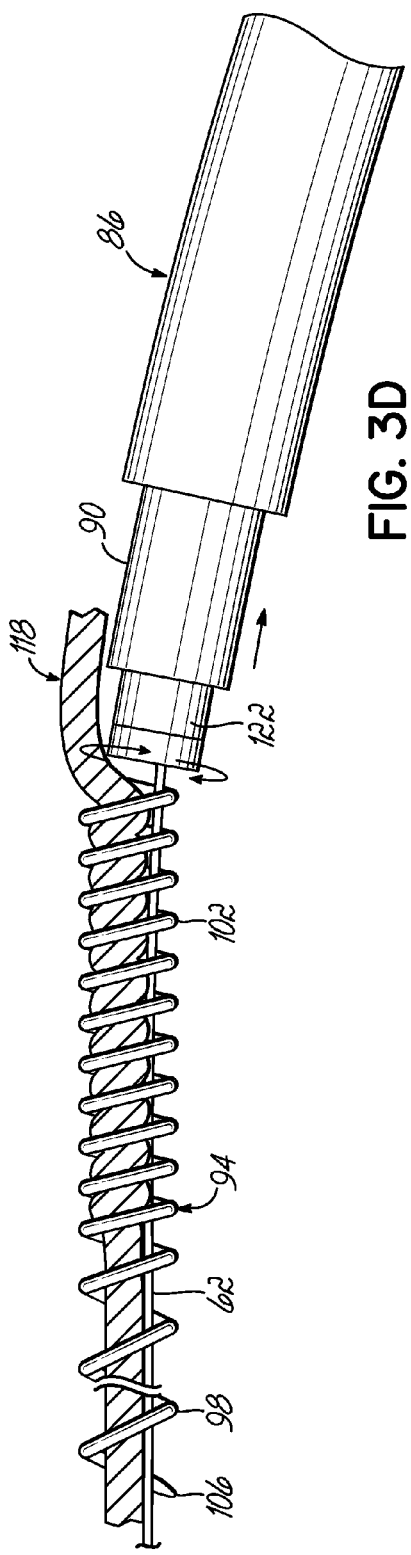
Figure 3E:
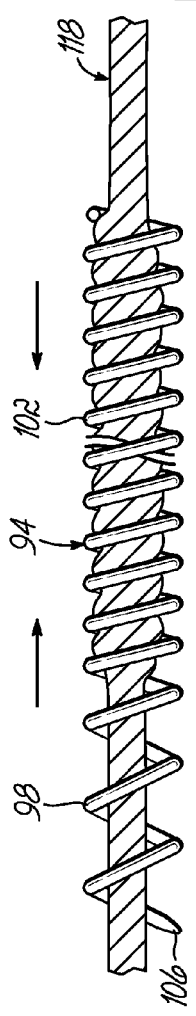

As the proximal end of the helical fastener 94 reaches the tissue 118, a hub 122 of the coil delivery device 126 begins to emerge from the delivery sheath 90, as shown in FIG. 3D. After the helical fastener 94 is fully loaded onto the tissue 118, the proximal portion 102 of the helical fastener 94 is uncoupled from the hub 122 in a manner described in greater detail below. The guide catheter 86, delivery sheath 90, coil delivery device 126, and guide-wire 62 are then retracted from the surgical site leaving the helical fastener 94 in position over the now plicated tissue 118, as shown in FIG. 3E.

The details of the coil deployment device 126 will now be described in detail and with particular reference to FIGS. 4A-4C. The coil deployment device 126 can include a torque coil 130 comprised of three alternating layers of coil 134, 138, 142. The three alternating layers of coil 134, 138, 142 increase the torque capacity of the deployment device over the distance between the arterial access site and the surgical site. Suitable torque coils 130 can include those commercially available, for example those by Asahi Intecc Co., Ltd. The three layers of coil 134, 138, 142 can be constructed, in one embodiment, from three layers of 0.1524 mm (0.006 inch) wire where the first layer is wound in a clockwise direction, the second layer is wound in the counter-clockwise direction, and the third layer is wound in a clockwise direction. The wire can be stainless steel or other known metal alloys capable of maintaining the necessary torque capacity while being surgically adaptable.

The distal end of the torque coil 130 is equipped with the hub 122, which can be welded, or otherwise fixed, to the distal end of the torque coil 130. As illustrated, the hub 122 includes an adapter cup 146 having a plurality of internal threads 150 approximately matching the pitch of the proximal portion 102 of the helical fastener 94. The internal threads 150 allow the helical fastener 94 to be threadably engaged into the adapter cup 146. As shown in FIG. 4A, the adapter cup 146 defines a hollow interior space that receives the helical fastener 94 and is defined by a peripheral outer wall. The internal threads 150 are formed along the inner surface of the peripheral outer wall. The hub 122 includes a stop 123 that is in the form of a floor that is defined between the peripheral outer wall.

In use, the adaptor cup 146 of the coil deployment device 126 is pre-loaded with the proximal portion 102 of the helical fastener 94. The coil deployment device 126, leading with the adaptor cup 146 and helical fastener 94, are backloaded into the delivery sheath 90, which are then backloaded, as a unit, into the guide catheter 86 (FIG. 1), and along the guide-wire 62. The coil deployment device 126 and delivery sheath 90 are advanced to the surgical site.

As illustrated in FIG. 4B, the tissue 118 to be plicated is larger in diameter than the helical fastener 94. Accordingly, the guide-wire 62 can be at least partially embedded within the tissue 118. After the helical fastener 94 and delivery sheath 90 emerge from the guide catheter 86, the physician can advance the distal tip 106 of the helical fastener 94 slightly beyond the delivery sheath 90 to engage the tissue 118. By rotational advancement, the distal tip 106 and the distal portion 98 of the helical fastener 94 are advanced into the surrounding tissue 118. The rotating advancement continues until the proximal portion 102 of the helical fastener 94 is within the tissue 118, which begins to plicate.

In FIG. 4C, the physician begins disengaging the proximal portion 102 of the helical fastener 94 from the coil deployment device 126. To disengage, the physician reverses the direction of the rotation as shown by arrows 148. Because the helical fastener 94 is more tightly engaged to the tissue 118 than the adaptor cup 146, the reversed rotation causes the helical fastener 94 to decouple from the coil deployment device 126. The coil deployment device 126, guide catheter 86, and guide-wire 62 are then retracted from the surgical site.

It is envisioned that a coil deployment device 152 can be constructed to allow for some retraction of the helical fastener 94 from the tissue 118. In one embodiment suitable for retraction, the hub 122 of the coil deployment device 152 includes a collet 154, as shown in FIGS. 5A-5C. The collet 154 includes at least two deflectable arms 158 connected to the hub 122 by elastic members 162. The internal surface of the deflectable arms 158 receives the helical fastener 94 and can include dentate structures 160 to grasp the proximal portion 102. The elastic members 162 can be springs, or similar structures, and are preferably arranged to bias the deflectable arms 158 open.

In use, the proximal portion 102 of the helical fastener 94 is inserted into the deflectable arms 158 which are then loaded into the delivery sheath 90 until the deflectable arms 158 are constrained within the delivery sheath 90 and grasp the proximal portion 102. This constraint maintains the proximal portion 102 of the helical fastener 94 within the collet 154. The coil deployment device 152 and delivery sheath 90 are then advanced to the surgical site. So long as the deflectable arms 158 are constrained within the delivery sheath 90, the proximal portion 102 of the helical fastener 94 is engaged within the collet 154 of the coil deployment device 152 and the physician can advance or retract the helical fastener 94 with respect to the tissue 118 by changing the direction of rotation.

FIG. 5B illustrates the release of the helical fastener 94 from the coil deployment device 152 after the helical fastener 94 has been fully advanced into the tissue 118. To release the helical fastener 94, the physician advances the collet 154 beyond the distal end of the delivery sheath 90 such that the elastic members 162 bias the deflectable arms 158 outwardly. The physician can then retract the delivery sheath 90, the coil deployment device 152, and the guide catheter 86 from the surgical site, as shown in FIG. 5C.

Release of the helical fastener 94 from the collet 154 can alternatively be accomplished by retracting the delivery sheath 90 from the collet 154.

Figure 6A:
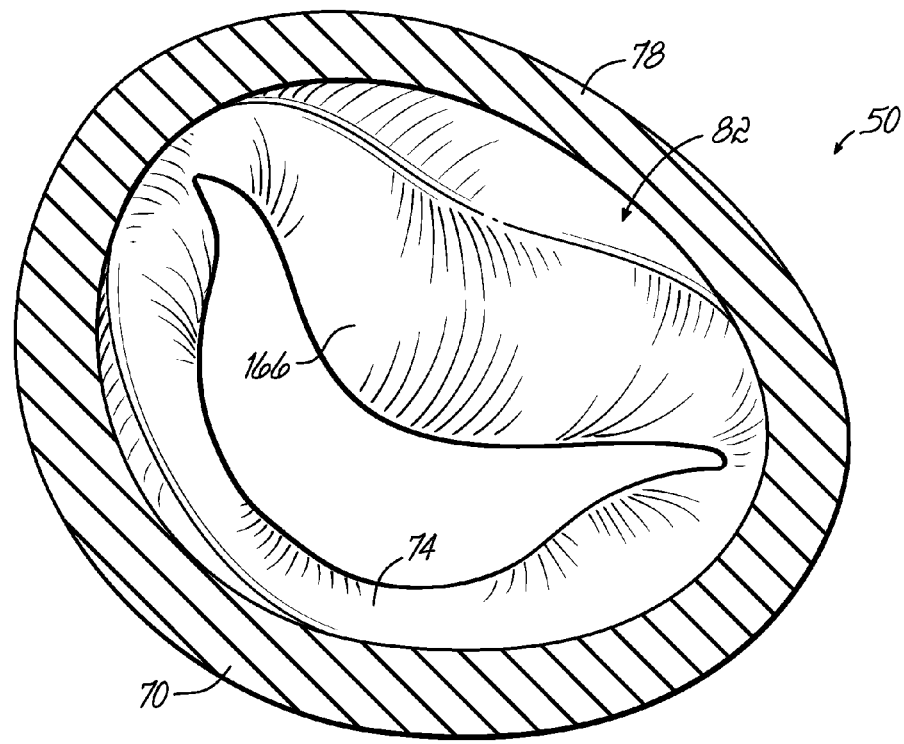
FIGS. 6A-6B are top plane views illustrating the mitral valve from the left ventricle before and after tissue plication with the helical fastener.
Figure 6B:
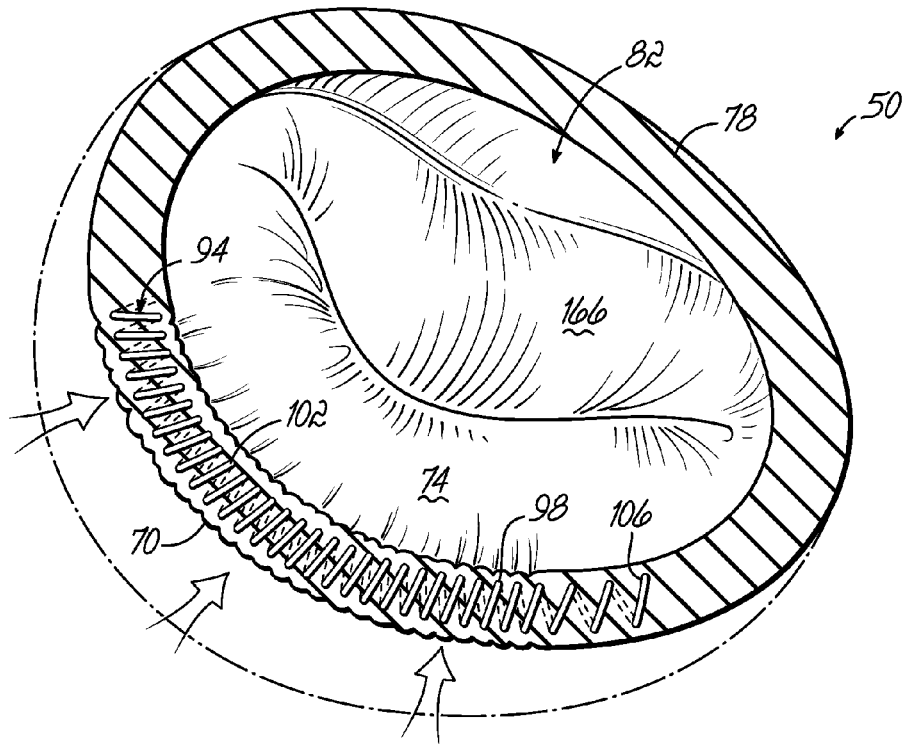

FIGS. 6A and 6B illustrate the changes in the mitral valve 50 due to plication of the tissue 118 by the helical fastener 94. FIG. 6A shows the mitral valve 50 before the helical fastener 94 is implanted where the posterior leaflet 74 is loose, does not coapt to the anterior leaflet 166, and can potentially prolapse into the left atrium 82. After the helical fastener 94 is implanted, as shown in FIG. 6B, the posterior annulus 70 is plicated and reshaped such that the circumference of the posterior annulus 70 and the septal-lateral dimension are both decreased. This pulls the posterior leaflet 74 toward the anterior leaflet 166 and allows the leaflets 74, 166 to fully coapt, thus increasing the efficiency of the mitral valve 50.

Figure 7A:
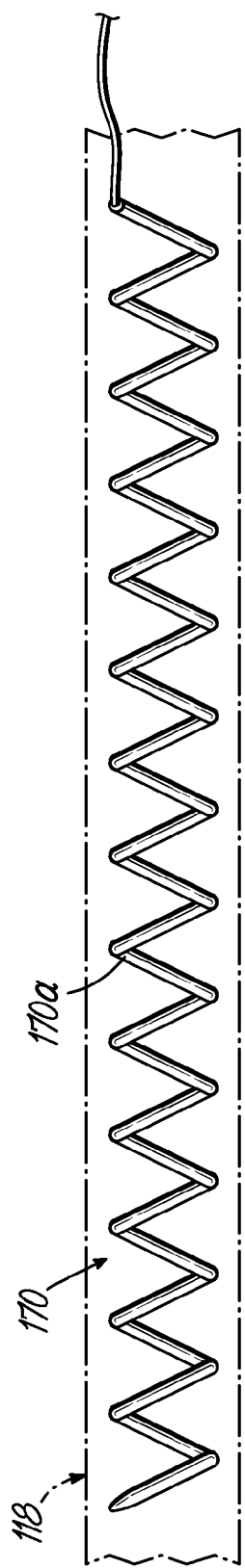
FIGS. 7A-7B are elevational views of an alternative embodiments of the helical fastener.
Figure 7B:
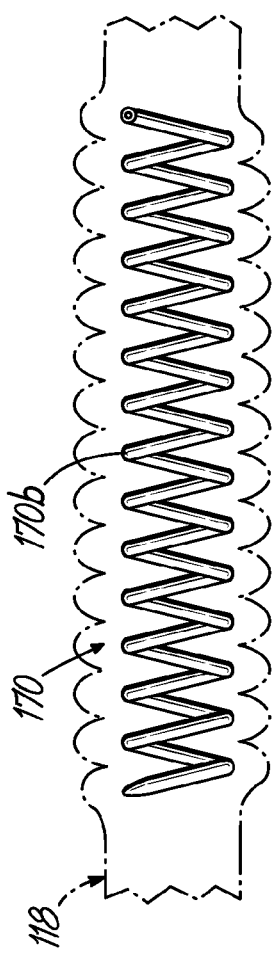

In one alternate embodiment, illustrated in FIGS. 7A and 7B, the tissue plication device can include a helical fastener 170 having a first configuration 170a with a first pitch (FIG. 7A) that is capable of being converted to a second configuration 170b with a second pitch (FIG. 7B) when a stimulus is applied. For example, the first pitch can be greater than the second pitch. When the stimulus is applied, the helical fastener 170 shortens and plicates the tissue 118. Suitable stimuli can include, but should not be limited to, thermal energy, magnetic energy, chemical reaction, mechanical energy, or combinations thereof, and can depend on factors such as the particular material(s) used in constructing the helical fastener 170. Suitable materials can include, in addition to the materials described previously, any shape memory material. Suitable materials can thus include metal alloys such as nickel titanium alloys, cobalt nickel aluminum alloys, titanium palladium, copper aluminum nickel; or non-metal polymers, such as VERIFLEX by Cornerstone Research Group, Inc. In some embodiments, the helical fastener material could be selected for its thermal response to temperatures that are approximately body temperature, i.e. greater than about 35.5° C. (96° F.).

In use, the helical fastener 170 is directed into the tissue 118 in a manner consistent with the methods described in detail above. After the helical fastener 170 is fully inserted within the tissue 118, the physician can apply the necessary stimulus to cause the helical fastener 170 to convert from the first to the second configurations 170*a*, 170*b*. This conversion causes the length of the helical fastener 170 to decrease, which plicates the tissue 118.

In another embodiment, not specially illustrated herein, the helical fastener is constructed such that the first configuration has a smaller pitch than the second configuration. The stimulus is applied to the helical fastener before introducing the helical fastener to the tissue. The helical fastener in the second configuration is directed and advanced into the tissue. Once the helical fastener is within, or surrounds, the tissue, the stimulus is removed and the helical fastener converts to the first configuration, thereby plicating the tissue.

In still other embodiments, the helical fastener can be constructed to have particular thermodynamic properties that affect the rate at which the helical fastener absorbs thermal energy. For example, a first helical fastener constructed from a nickel titanium alloy having an outer diameter of 1.016 mm (0.040 inches) will have a greater mass than a second helical fastener constructed with an outer diameter of 0.508 mm (0.020 inches). Accordingly, one skilled in the art would understand that the larger first helical fastener would require a greater amount of thermal energy than the smaller helical fastener to achieve a similar response.

Other methods of altering the thermodynamic response of the helical fastener can include the application of an insulator coating, such as polytetrafluoroethylene, or ceramic materials, such as metal oxides (titanium oxide or calcium oxide), onto the helical fastener. Helical fasteners including these insulator coatings would absorb thermal energy at a slower rate than a similarly constructed helical fastener without the insulating coating material. Insulating coating materials can be added to the helical fastener construction by applying a shrink wrap tubing, dip coating processes, spray coating processes, thermal spray coating processes, or other known methods within the art.

While the helical fasteners described herein have been primarily shown in use with the mitral valve, it would be understood that other anatomical features can benefit from plication by the helical fastener. For example, the mitral valve could be plicated from the left atrium. Additionally, other openings through tissues could be plicated, including other heart valves.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims. What is claimed is:

The invention claimed is:

1. A method of plicating a tissue with a tissue plication device comprising a helical fastener having a distal portion with a first pitch, a proximal portion with a second pitch that is smaller than the first pitch, and a distal tip, the method comprising:
    providing a coil deployment device having a hub formed at a distal end, the hub having a hollow interior space defined by a peripheral wall that includes threading formed on an inner surface of the peripheral wall and a stop in the form of a floor that extends between the peripheral wall proximal to but separate from the threading and prevents the helical fastener from further movement in a proximal direction, the stop having a through opening formed therein for allowing passage of a guide wire, wherein the floor comprises a wall that extends radially inward relative to the threading to form a surface against which the helical fastener seats;
    engaging a proximal end of the proximal portion of the helical fastener with the threading so as to cause the proximal portion to seat against the stop;
    introducing the distal tip into the tissue;
    advancing the distal portion of the helical fastener into the tissue by rotating the distal end of the coil deployment device;
    continuing the advancing until the proximal portion of the helical fastener occupies a space previously occupied by the distal portion, thereby plicating the tissue;
    disengaging the proximal end of the proximal portion of the helical fastener with the threading.

2. The method according to claim 1 further comprising:
    advancing a guide-wire into the tissue before introducing the distal tip of the helical fastener, whereby the helical fastener is directed over the guide-wire and into the tissue.

3. The method according to claim 2, wherein the advancing includes rotating the helical fastener about the guide-wire.

4. The method according to claim 1, wherein the tissue is a posterior annulus of the mitral valve.

5. The method according to claim 4, wherein the helical fastener is percutaneously directed with at least one catheter through the aortic arch to the posterior annulus within the left ventricle.

6. The method according to claim 4, wherein the helical fastener is percutaneously directed with at least one catheter into the right atrium, across an intra-atrial septum, and to the posterior annulus within the left atrium.

7. The method according to claim 4, wherein the helical fastener is percutaneously directed with at least one catheter through a circumflex artery.

8. The method according to claim 1, wherein the introducing and advancing of the helical fastener into the tissue includes causing the helical fastener to at least partially extend around the tissue.

9. The method according to claim 1, wherein the distal end of the coil deployment device defines a cup and the threading is provided on an interior wall of the cup.

10. A method of plicating a tissue with a tissue plication device comprising a helical fastener having a first configuration with a first pitch, a second configuration with a second pitch that is smaller than the first pitch, and a distal tip, the method comprising:
    providing a coil deployment device having a hub formed at a distal end, the hub having a hollow interior space defined by a peripheral wall that includes threading formed on an inner surface of the peripheral wall and a stop in the form of a floor that extends between the peripheral wall proximal to but separate from the threading and prevents the helical fastener from further movement in a proximal direction, the stop having a through opening formed therein for allowing passage of a guide wire, wherein the floor comprises a wall that extends radially inward relative to the threading to form a surface against which the helical fastener seats;
    engaging a proximal end of the proximal portion of the helical fastener with the threading so as to cause the proximal portion to seat against the stop;
    introducing the distal tip into the tissue;

advancing the helical fastener into the tissue by rotating the distal end of the coil deployment device, wherein the helical fastener is in the first configuration;

converting the helical fastener from the first configuration to the second configuration by applying a stimulus to the helical fastener, thereby plicating the tissue; and disengaging the proximal end of the proximal portion of the helical fastener with the threading.

11. The method of plicating a tissue according to claim 10, wherein the stimulus is a thermal energy, a magnetic energy, a chemical reaction, a mechanical energy, or a combination thereof.

12. The method according to claim 10 further comprising:
advancing a guide-wire into the tissue before introducing the distal tip of the helical fastener, whereby the helical fastener is directed over the guide-wire and into the tissue.

13. The method according to claim 10, wherein the tissue is a posterior annulus of the mitral valve.

14. The method according to claim 13, wherein the helical fastener is percutaneously directed with at least one catheter through the aortic arch to the posterior annulus within the left ventricle.

15. The method according to claim 13, wherein the helical fastener is percutaneously directed with the at least one catheter into the right atrium, across an intra-atrial septum, and to the posterior annulus within the left atrium.

16. The method according to claim 13, wherein the helical fastener is percutaneously directed with the at least one catheter through a circumflex artery.

17. The method according to claim 10 further comprising:
removing the stimulus, thereby converting the helical fastener from the second configuration to the first configuration.

18. The method according to claim 10, wherein the helical fastener includes an insulator coating that alters a rate of thermal energy absorption by the helical fastener.

19. The method according to claim 10, wherein the introducing and advancing of the helical fastener into the tissue includes causing the helical fastener to at least partially extend around the tissue.

20. The method according to claim 10, wherein the distal end of the coil deployment device defines a cup and the threading is provided on an interior wall of the cup.

21. A method of plicating a tissue with a tissue plication device comprising a helical fastener having a first configuration with a first pitch, a second configuration with a second pitch that is larger than the first pitch, and a distal tip, the method comprising:

converting the helical fastener to the second configuration;

providing a coil deployment device having a hub formed at a distal end, the hub having a hollow interior space defined by a peripheral wall that includes threading formed on an inner surface of the peripheral wall and a stop in the form of a floor that extends between the peripheral wall proximal to and separate from the threading and prevents the helical fastener from further movement in a proximal direction, the stop having a through opening formed therein for allowing passage of a guide wire, wherein the floor comprises a wall that extends radially inward relative to the threading to form a surface against which the helical fastener seats;

engaging a proximal end of the proximal portion of the helical fastener with the threading so as to cause the proximal portion to seat against the stop;

introducing the distal tip into the tissue;

advancing the helical fastener into the tissue by rotating the distal end of the coil deployment device, wherein the helical fastener is in the second configuration;

converting the helical fastener from the second configuration back to the first configuration, thereby plicating the tissue; and disengaging the proximal end of the proximal portion of the helical fastener with the threading.

22. The method according to claim 21, wherein the introducing and advancing of the helical fastener into the tissue includes causing the helical fastener to at least partially extend around the tissue.

23. The method according to claim 21, wherein the distal end of the coil deployment device defines a cup and the threading is provided on an interior wall of the cup.

* * * * *